Jan. 15, 1946. A. R. CHENOWETH Plant Pat. 667
AVOCADO TREE
Filed Feb. 9, 1945
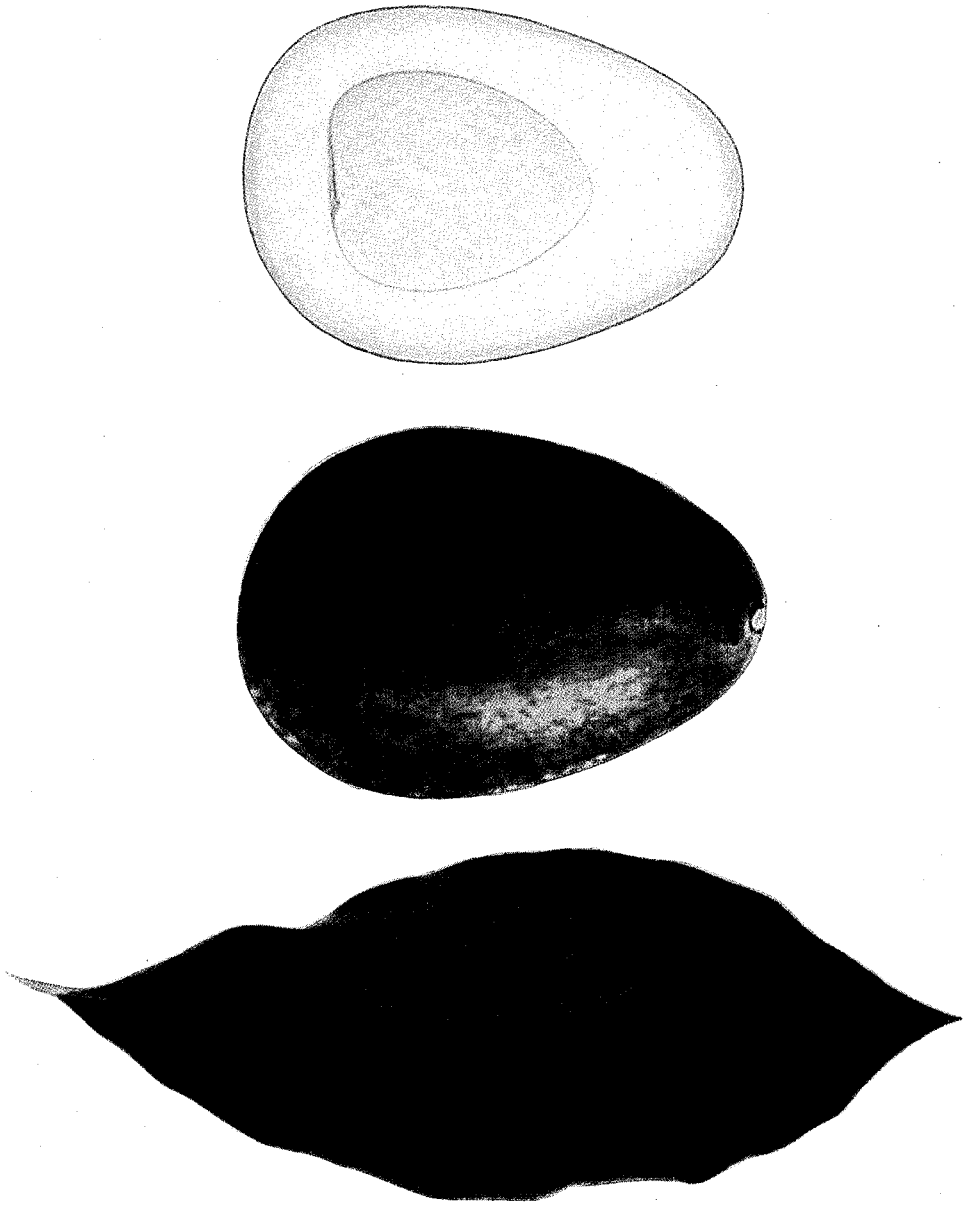
INVENTOR
Arthur R. Chenoweth
By Orville M. Kile
Plant Patent Agt.

Patented Jan. 15, 1946

Plant Pat. 667

UNITED STATES PATENT OFFICE

667

AVOCADO TREE

Arthur R. Chenoweth, San Diego County, Calif.

Application February 9, 1945, Serial No. 576,961

1 Claim. (Cl. 47—62)

My present discovery relates to a new and distinct variety of avocado tree which originated as a chance Mexican seedling which first fruited on my farm some years ago. I have grafted a number of trees from this original seedling and from these grafted trees took grafts to topwork other trees. So I now have both second and third generation grafted trees of my new variety—all of which are now bearing.

The outstanding features of my new variety are its early season of fruit maturity, its constancy in bearing good crops, and the high oil content and the unusual rich nutty flavor of the fruit. All of these features have proved to be permanent in the succeeding generations of grafted trees. Crops have usually been abundant although this year it was rather light. However the trees of the variety bear a good average crop each year rather than bearing in alternate years like Fuerte and other similar known varieties do.

My new variety is like the Fuerte in many respects. One great difference, however, is its ripening season. My variety begins to ripen its fruits in September and the season extends through November, the harvest being concluded at about the time the harvest of Fuerte gets under way. Since Fuerte is the principal commercial variety in this area, my new variety would lengthen the avocado marketing season here by at least two months. This would be very desirable both from the standpoint of the grower and of the consumer.

The accompanying illustration shows a leaf, the outside of a fruit, and a fruit in cross-section, all in approximately their true colors.

Following is a detailed description of my new variety of avocado tree, color references being to Ridgway's Color Standards and Nomenclature.

*The tree*

Growth habits: Upright, vigorous, spreading somewhat like Fuerte but more symmetrical and foliage more compact.

Hardness: Variety can be classified as hardy since it is fully as hardy as Fuerte. It blooms in the spring after the period when frosts may be expected so the bloom is not damaged by cold.

Plant maturity: Tree fruits at an early age. The grafted plants bear fruit at two or three years after grafting, so the variety may be called precocious.

Fruiting habits: This variety produces a good crop regularly each year instead of in alternate years as many varieties do. Usually the crop is abundant although some years it is only moderate.

Ripening season: Fruit harvesting season is early, beginning about the first of September and continuing through November.

Foliage:

*Amount and arrangement.*—Abundant and rather compact.

*Size of leaves.*—7¼ to 7½ inches long by 2¾ to 3½ inches wide.

*Shape of leaves.*—Elliptical with acuminate apex and base.

*Color of leaves.*—Dark green.

*Veins.*—Parallel from midrib to margin; rather prominent.

*The Fruit*

Size: Small compared to some varieties. Average weight is 6 or 7 ounces. Measures about 4 inches long, 2½ to 3 inch diameter and 8 inch circumference at largest part.

Form: Asymmetrical pyriform. Uniform.

Skin: Very thin, easily removed when ripe. Basic skin color Forest Green (Pl. XVII) to Dark Green (Pl. XVIII), frequently with dots of reddish brown irregularly dispersed over the surface.

Flesh: There is very little fibre in the flesh and the rich, nutty flavor is considered by experts to be better than that of the variety Fuerte. Oil content is very high, usually 20 to 21 percent at ripening. Color of the flesh is rich yellow between Straw Yellow (Pl. XVI) and Naples Yellow (Pl. XVI), except that there is a one-eighth inch rim of light green flesh next to the skin.

Seed: Medium in size. Average weight is 2 ounces, length 2 inches, diameter 1¾ inches and circumference 5 inches. Smooth. Easily removable when fruit is ripe.

Having thus disclosed my discovery, I claim:

The new and distinct variety of avocado tree substantially as shown and described, characterized particularly by its earily ripening season, its consistent bearing of good crops each year, and the very rich, nutty flavor and high oil content of its fruits.

ARTHUR R. CHENOWETH.